United States Patent [19]
Wagner et al.

[11] 4,205,058
[45] May 27, 1980

[54] COLUMN CHROMATOGRAPHY SPECIFIC BINDING ASSAY METHOD AND TEST KIT

[75] Inventors: Daniel B. Wagner; Anthony J. Pick; Judith Feingers, all of Jerusalem, Israel

[73] Assignee: Ames-Yissum, Ltd., Jerusalem, Israel

[21] Appl. No.: 852,105

[22] Filed: Nov. 16, 1977

[30] Foreign Application Priority Data

Jan. 28, 1977 [IL] Israel ........................................ 51354

[51] Int. Cl.$^2$ ..................... G01N 33/16; A61K 43/00; B65D 81/32
[52] U.S. Cl. ..................................... 424/1; 23/230 B; 424/12; 422/61
[58] Field of Search ....................... 424/1, 12; 422/61; 23/230 B

[56] References Cited
U.S. PATENT DOCUMENTS 4,094,647  6/1978  Deutsch et al. ................. 23/230 B Primary Examiner—Benjamin R. Padgett
Assistant Examiner—Christine M. Nucker
Attorney, Agent, or Firm—Andrew L. Klawitter

[57] ABSTRACT

A specific binding assay method and test kit for determining a ligand, such as an antigen or antibody, in, or the ligand binding capacity of, a liquid medium, particularly a body fluid such as serum, wherein the unknown ligand competes with a labeled component, such as a radio labeled form of the ligand or of a binding analog of the ligand, for binding with a binding partner, with the improvement that separation of the resulting bound-species and free-species of the labeled component is accomplished by drawing the liquid reaction mixture into a column of an adsorbent material selective for one of the two species. Separation results by immobilization of the selected species at the beginning portion of the adsorbent column while the other species is transported farther along the column by advance of the reaction mixture. The present method is manipulatively simple and advantageous over the many known techniques; finds special application to radioimmunoassay, particularly for detecting low molecular weight ligands; and is readily adaptable to automation.

44 Claims, 8 Drawing Figures

COLUMN CHROMATOGRAPHY SPECIFIC BINDING ASSAY METHOD AND TEST KIT

BACKGROUND OF THE INVENTION

1. Field of the Invention

This invention relates to the quantitative determination of substances in or characteristics of liquid media, including body fluids such as serum, based on specific binding assay techniques. In particular, the invention is directed to the detection of antigens or haptens based on immunoassay techniques involving the use of labeled reagents, such as radiolabeled reagents. The present invention provides an improved method of performing the separation of bound- and free-label inherent in heterogeneous specific binding assays.

2. Description of the Prior Art

A living system is able to detect, recognize and respond to the presence of foreign material (antigen) such as protein, virus, bacteria, and so forth, within that system. This response takes, inter alia, the form of producing an antibody specific for the particular antigen. There then occurs a specific reaction between the antibody and the antigen to form a complex. An antibody once produced is also capable of binding a hapten, i.e., a relatively small and simple compound which may be the determinant group of a given antigen, which hapten is capable of binding with the specific antibody but incapable itself of giving rise to the production of an antibody, unless it is bound to an antigenic carrier.

The binding interaction between an antigen or a hapten and its antibody is specific and sensitive. Other types of materials that participate in similar specific and sensitive binding interactions are enzymes and their substrates; materials such as hormones, vitamins, metabolites and pharmacological agents, and their receptors and binding substances; and other substances known in the science. These specific and sensitive binding reactions have given rise to a rapidly emerging analytical technique known as the specific binding assay technique. In one such type of assay method, the substance, or group of substances, to be determined (herein referred to as "ligand") in a liquid sample is placed in competition with a labeled form of the ligand or of a binding analog thereof for binding to a binding reagent. Where a radioactive label is used and the binding reagent is an antibody, the method is known as a radioimmunoassay method. Recently, several alternative labeling materials have been reported for replacement of radioisotopes, including enzymes, coenzymes, enzyme substrates, enzyme modulators such as inhibitors and allosteric effectors, fluorescent molecules, luminescent molecules, and others. For illustrative purposes, the discussion which follows describes one particular type of specific binding assay technique, a competitive binding radioimmunoassay technique.

This system consists of antigen or hapten labeled with a radioactive marker, unlabeled native antigen (in the test sample) and specific antibody whereby there is competition between the unlabeled antigen and the labeled antigen for binding to a limited amount of antibody. Hence, the greater the concentration of unlabeled antigen from the test sample in the system, the less the labeled antigen will be bound by the antibody. This may be diagrammatically represented as follows:

LABELED + SPECIFIC + UNLABELED
ANTIGEN   ANTIBODY   ANTIGEN

*Ag        Ab         Ag $\updownarrow$

LABELED AND UNLABELED
ANTIGEN-ANTIBODY COMPLEX
(*Ag − Ab) + (Ag − Ab)

If the concentration of labeled antigen and antibody is fixed and the only variable is the level of unlabeled antigen, it becomes possible to establish an assay system for measuring the unknown level of unlabeled antigen by physically separating the antigen-antibody complex from the remaining free antigen (both labeled and unlabeled). The radioactivity of the unknowns is compared with a standard curve plotting of the values given by a range of known amounts of the antigen treated in the same manner.

There are many known procedures for separating the free unbound antigen or hapten from the complex antigen-antibody. One method known as chromatoelectrophoresis combines techniques of paper chromatography and paper electrophoresis. Paper with a high affinity for the free antigen (such as Whatman 3 MM, Whatman 3 MC and DEAE paper) are used as carriers. While this technique is discriminative and has been used in the assay of insulin, growth hormone, glucagon, parathyroid hormone, thyroid stimulating hormone and other peptide hormones, it has a number of prominent disadvantages which limits its use. A limited amount of material may be applied to the adsorbent, and the separation is both laborious and time-consuming.

Another known procedure, which has been proposed for the assay of the above-mentioned peptide hormones, makes use of ascending paper-wick chromatography, e.g., on Whatman 3MC and DE-cellulose paper or on paper loaded with weak ion-exchange resins. Orskov, Scand. J. Clin. Lab. Invest. 20: 297(1967). This method too has the disadvantage that the amount of sample which can be applied to the lower tip of the paperwick is comparatively small. It is further necessary in this technique to dry the paper (sometimes even twice) and to cut it before the counting, which is disadvantageous for applying the method to the assay of a large number of samples by mechanical means. It is also most significant that in more than a decade this known method has not been cited as being of any importance in the literature and has not been applied to the radioimmunoassay of relatively low-molecular weight haptens.

By another known method the antigen-antibody complex is precipitated by salts, organic material or solvents under conditions that do not affect the free antigen. Among the salts, materials and solvents used are: ethanol, acetone, sodium sulfate, ammonium sulfate, dioxane, trichloroacetic acid, polyethylene glycol, and so forth. The use of salts, solvents or organic materials has the advantage that the separation is immediate, and a second incubation is not necessary. However, the chemical precipitation technique may cause the co-precipitation of other proteins, often causing an incomplete separation of the two fractions.

There is also known the double antibody technique, which is widely used for the separation of the bound and the free antigen. By this method a second antibody that was raised against the first antibody is used to precipitate the primary antigen-antibody complex. For example, if the first antibody was raised in a rabbit then the second antibody may be an antiserum to rabbit gammaglobulin raised in goats. One disadvantage of this technique is that the use of a second antibody introduces an additional incubation. Specific binding assay methods employing a double antibody separation technique are described in U.S. Pat. Nos. 3,839,153 and 3,872,225.

Furthermore, there are known various solid-phase techniques for the separation of free and bound antigen. These techniques make use of antibodies covalently bound or physically adsorbed to an insoluble matrix (immunosorbents), such as bentonite, cellulose, bromacetyl cellulose, the crosslinked dextrans (Sephadex), sepharose, plastic (non-cross-linked polystyrene or polypropylene) beads, Enzacryl AA, nitro-cellulose membranes, and so forth. The formed antibody-antigen complex is held by the solid phase and the bound fraction is thus directly separated from the free fraction.

By yet another method the free (unbound) antigens are bound to adsorbents which then can be precipitated by centrifugation. Powdered talc (magnesium silicate), Kaolin (aluminum silicate), QUSO (microgranules of silica), cellulose powder, and so forth, are some of the simple adsorbents used. Many separations are performed by using adsorbent charcoal coated with dextran. The dextran behaves rather like a sieve which allows the smaller molecules of free antigen to pass and these are then bound by the charcoal, leaving the bound antigen in solution, after the charcoal has been removed by centrifugation or filtration.

It is also known to use ion exchange or other types of resins to bind free antigens by electrostatic forces and this method has been used so far mainly for the determination of small molecules such as thyroid hormones (T-3 and T-4). Examples of this type of methodology are described in U.S. Pat. Nos. 3,659,104; 3,710,117 and 3,961,894.

One technique of this type used for the separation of the antigen-antibody complex from free antigen employs a column packed with material which preferentially adsorbs either the free antigen or the antigen-antibody complex. The incubated aqueous reaction mixture is applied to the head of such a column and the column is then eluted. The radioactivity of either the column or the eluate is then determined and the content of the antigen in the starting solution is calculated from the count.

In practice it has been found that this technique is somewhat cumbersome and not well suited for the rapid performance of a large number of radioimmunoassays with the aid of mechanical means. One of the reasons for this is that it is necessary to wash the non-adsorbed component completely out of the column which takes time and requires a relatively large amount of buffer solution.

It is an object of the present invention to provide an improved specific binding assay method in which the separation of the bound-species of the labeled component and the free-species thereof is accomplished in a novel manner which is more advantageous than the separation methods known in the art.

SUMMARY OF THE INVENTION

Accordingly the present invention provides, in a specific binding assay method for determining a ligand in or the ligand binding capacity of a liquid medium, wherein for determining said ligand, said liquid medium is combined with assay reagent means comprising (i) as labeled component, said ligand or a binding analog thereof incorporated with a label and (ii) a binding reagent for said ligand; or wherein for determining the ligand binding capacity of said liquid medium suspected of containing a binding agent for said ligand, said liquid medium is combined with assay reagent means comprising, as labeled component, said ligand or a binding analog thereof incorporated with a label, thereby to form a binding reaction mixture having a bound-species as said labeled component bound to said binding reagent and a free-species as said labeled component not bound to said binding agent;

wherein said bound-species and said free-species are separated, and wherein said label is measured in one of the separated species;

the improvement which comprises accomplishing said separation of said bound-species and said free-species by drawing at least a portion of said binding reaction mixture into a column of an adsorbent material selective for one of said bound-species and said free-species whereby said bound-species and said free-species are separated along said column.

In preferred embodiment, the column of adsorbent is in the form of an elongated tube packed with a sufficient quantity of a capillarily absorbent form or type of such adsorbent to effect complete take up of all of the binding reaction mixture upon contact of one end of such tube with such mixture. Preferably the adsorbent column is kept in a vertical position during the capillary absorption process resulting in an ascending chromatographic separation. To enhance separation of the bound- and free-species along the column, a volume of an inert liquid such as a buffer may be allowed to be absorbed into the adsorbent column after all of the reaction mixture has been absorbed.

The principle of the separation technique is that the adsorbent is selective for one of the bound- and free-species, usually the latter, and will bind non-specifically therewith to substantially immobilize that species against the movement of the reaction mixture through the adsorbent column. The other species will of course be carried by the flow of the reaction mixture away from the beginning portion of the column where the immobilized species is, thereby effecting inherent separation of the bound- and free-species.

The great advantage of this separation technique is that the necessary separation step is reduced to the simple task of contacting the reaction mixture with the column adsorbent for a sufficient period of time to permit the necessary absorption of the liquid into the adsorbent. Further, the resulting column carrying the separated bound- and free-species is quite convenient for subsequent measuring steps, particularly where the label is radioactive. Even further, using the present column chromatography method, the mechanical steps of initiating the separation step and removing the separation device to a measuring location are readily adaptable to automation. An additional advantage is afforded when the label used is of a hazardous type, such as a radioactive label, since all of the label added in forming the reaction mixture ends up in a single, readily disposable device - the adsorbent column.

The present invention separation method is applicable generally to the specific binding assay detection of ligands, such as the radioimmunoassay detection of antigens and haptens including thyroxine (T-4) and digoxin, and to the assay of sample binding capacity for various ligands, such as the serium binding capacity for triiodothyronine (T-3).

DESCRIPTION OF THE PREFERRED EMBODIMENTS

Figure 1:
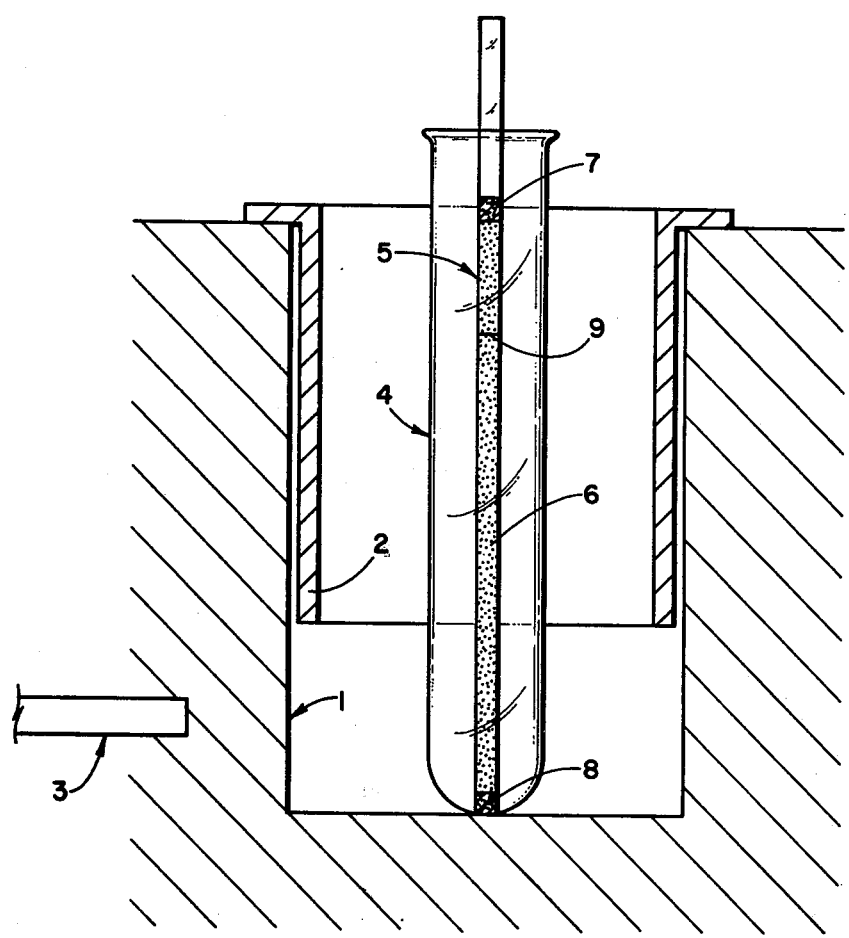
FIG. 1 is a cross-sectional view of a well of a counter in the course of performance of a measurement in accordance with a preferred embodiment of the invention.

In the context of this disclosure, the following terms shall be defined as follows: "ligand" is the substance, or group of substances, whose presence or the amount thereof in a liquid medium is to be determined; "binding agent for the ligand" is any substance, or group of substances, which has a specific binding affinity for the ligand to the exclusion of other substances; and "binding analog of the ligand" is any substance, or group of substances, which behaves essentially the same as the ligand with respect to the binding affinity of the binding agent for the ligand.

The separation of the bound- and free-species of the labeled component in specific binding assays by selective adsorption is well-known. According to the prior art methods, interaction between the binding reaction mixture and the adsorbent is effected either by addition to the reaction mixture of the adsorbent in a powder, bead, or strip form followed by physical removal of the adsorbent such as by centrifugation or filtration or by withdrawal of the strip adsorbent; or by perculating and washing the reaction mixture downwardly under influence of gravity through a bed of the adsorbent whereby the effluent emerging from the bed contains only one of the bound- and free-species of the labeled constituent.

The present invention affords an improved separation technique employing a selective adsorbent in that the reaction mixture is drawn into a column of the adsorbent material such as by capillary action, as is preferred, or by means of external force such as a vacuum. While under some circumstances it may be necessary or desirable to draw only a portion of the reaction mixture into the adsorbent column, normally the volume of the reaction mixture and the capacity of the column will be selected so that the entire reaction mixture will be drawn into the adsorbent column. Selective adsorption of the bound- or free-species occurs immediately upon contact between the reaction mixture and the adsorbent at the beginning portion of the adsorbent column. However, the non-adsorbed species moves on along the column with the advancing solvents in the reaction mixture. Upon completion of the movement of the reaction mixture into the column, substantially all of the selectively adsorbed species has become immobilized in the beginning end region of the column whereas the other species is found towards the other end of the column.

Enhancement of separation between the bound- and free-species can be accomplished by following the take up of the reaction mixture by exposure of the beginning end portion of the column to a volume of a liquid inert with respect to the selective adsorption of the one species at the beginning end portion but which acts as further solvent to carry the other species further into the adsorbent column. In the usual case, this liquid is water or an aqueous buffer solution.

Since numerous adsorbents selective for one of the bound- and free-species are well documented in the published literature, it does not serve any useful purpose to set forth an exhaustive list here. The adsorbent column is preferably of a type which is capable of drawing the reaction mixture thereinto by capillary action. This can be accomplished by using an adsorbent which itself is capillarily absorbent or by mixing the adsorbent with a capillarily absorbent material, or both. Particularly useful adsorbents have been found to include cross-linked polyvinyl alcohol, cross-linked dextrans, starch, and silica gel. These adsorbents are appropriately hydrophilic and inert to aqueous reaction mixtures, and can be selected to preferentially adsorb the free-species of commonly performed binding assays.

The adsorbent column is preferably in the form of a bed of adsorbent contained within an elongated tube and supported at least at one end by retainer means previous to the reaction mixture. An example of a useful column device is a plastic tube (polypropylene or polystyrene) packed with a particulate form of the adsorbent held in place between porous disks of plastic, glass wool, or paper.

As a rule the volume of the reaction mixture used for the assay is small, e.g., of the order of 0.5 to 1 ml. The adsorbent column should be so dimensioned that the bulk of the non-adsorbed component becomes sufficiently removed from the bulk of the preferentailly adsorbed component which remains at the beginning portion so as to enable the selective measurement of the label specified. For example, where the body of adsorbent material is enclosed in a tube, the inner diameter of the tube may range from 0.1 to 1.0 cm and will preferably be around 0.5 cm. The intake tip of such a tube will advantageously have a constriction adapted to hold a plug of porous material, e.g., of glass wool, which serves as a retainer for the absorbent while being pervious to the aqueous reaction mixture. A practical length for such a tube may be from 5 to 10 cm.

In principle, the label may be any of those known in the art as discussed above, however, it is most advantageous to use a label which can be measured in the adsorbent column without removal of the adsorbent. For this system, the adsorbent is held in containing means transparent to the labeling characteristic. The use of radioactive labels, particularly gamma-emitting isotopes, fits well into this scheme. The art is replete with teachings concerning the use of such radiolabels as $^{125}$I, $^{131}$I, $^{57}$Co and so forth in binding assays. The present invention provides a separation means well suited for radioassays since the column device itself can be used in the measurement step and provides, upon the completion of the test, a disposable device containing all of the radioactivity used in the assay.

The selective measurement of the radioactivity of the intake region of the absorbent column is a simple operation due to the physical separation of the components on the column and the low radiation intensities of the radioactive labels preferably employed (mostly $^{125}$I at intensities not exceeding 200 kcpm). As a rule, a counter for the measurement of radioactivity comprises a so-called well, i.e., a recess or socket adapted to receive a sample to be measured. Beyond the lateral wall of that well there is located at least one detector. Where the distance between the nonadsorbed component and the adsorbed one is larger than the depth of the well, the selective measurement occurs automatically upon the introduction of the column into the well with the intake region inwards. Where this is not the case and the depth of the well is larger than the distance between the two components, it is possible to shield off that portion of the column containing the nonadsorbed component with a radioactivity opaque absorbing material, e.g., lead, so that the detector responds only to the radioactivity of the intake portion of the column. Such a shield will be shaped and dimensioned in accordance with the specific geometry of the contour and the sample used. The shield can be in the form of a plate or, most preferably, a cylindrical tube having an inner diameter only slightly larger than the column device.

As shown in FIG. 1, well 1 of the counter is partially shielded by tubular metal shield 2, e.g., of lead, mounted in a removable manner. In FIG. 1, shield 2 is schematically shown in close proximity to the wall of well 1, but, as pointed out above, shield 1 should most preferably fit closely around test tube 4 containing the sample. Facing the unshielded portion of well 1 is detector 3. Into the well there is inserted test tube 4 in which the incubation was originally carried out and from which the reaction mixture was drawn into tube 5 packed with selective absorbent 6. Absorbent 6 is retained by two retainer plugs 7 and 8, e.g., of glass wool as shown. In consequence of the take up of the reaction mixture by absorbent 6 in tube 5, the liquid has ascended up to boundary 9 and in this way the bulk of the nonadsorbed component has been transported to the region of well 1 which is shielded by shield 2 while the adsorbed component is retained in the lower intake region of tube 5 in the nonshielded portion of the well. In this way only the radioactivity of the intake region is selectively measured. If it is desired to measure the total radioactivity of the material in tube 5, shield 2 is withdrawn.

Radioactivity counters are also known in which a detector is located below the bottom wall of the well, in addition to the lateral detectors. If such a counter is used in the method of the present invention, care must be taken to shield off said detector located below the bottom of the well, in order to prevent it from picking up counts from the aligned non-adsorbed component which has migrated up into the adsorbent column.

The present assay method may be applied to the detection of any ligand for which there is a specific binding partner. The ligand usually is a peptide, protein, carbohydrate, glycoprotein, steroid, or other organic molecule for which a specific binding partner exists in biological systems or can be synthesized. The ligand, in functional terms, is usually selected from the group consisting of antigens and antibodies thereto; haptens and antibodies thereto; and hormones, vitamins, metabolites and pharmacological agents, and their receptors and binding substances. Specific examples of ligands which may be detected using the present invention are hormones such as insulin, chorionic gonadotropin, thyroxine, triiodothyronine, and estriol; antigens and haptens such as ferritin, bradykinin, prostaglandins, and tumor specific antigens; vitamins such as biotin, vitamin $B_{12}$, folic acid, vitamin E, and ascorbic acid; metabolites such as 3',5' adenosine monophosphate and 3',5' guanosine monophosphate; pharmacological agents such as dilantin, digoxin, morphine, digitoxin, and barbiturates; antibodies such as microsomal antibody and antibodies to hepatitis and allergens; and specific binding receptors such as thyroxine binding globulin, avidin, intrinsic factor, and transcobalamin.

In preferred embodiment, the detection of the ligand in the liquid medium, usually aqueous, is carried out by an improved radioimmunoassay method of the type wherein said aqueous medium is mixed with a radiolabeled form of said ligand or of a binding analog thereof and with an antibody for said ligand and the resulting reaction mixture is incubated to form a bound-species of said radiolabeled ligand or analog wherein such is bound to said antibody and a free-species of said radiolabeled ligand or analog wherein such is not bound to said antibody, wherein said bound-species and said free-species are separated, and wherein the radioactivity of one of said separated bound-species and said free-species is measured. The improvement of the present invention comprises accomplishing said separation of said bound-species and said free-species by contacting said reaction mixture with a column of a capillarily absorbent adsorbent material which is selective for one of said bound-species and said free-species and which is capable of drawing all of said reaction mixture thereinto by capillary action whereby said bound-species and said free-species are separated along said column.

From the total radioactivity (total count) and the radioactivity of the intake portion of the column (partial count) measured after the separation of the components, the percent retention is calculated by the following formula:

$$\text{percent retention} = \frac{\text{partial count}}{\text{total count}} \times 100$$

For the determination of unknown quantities of the ligand, it is first necessary to perform a series of assays with varying known amounts of ligand, thereby to establish a standard percent retention versus concentration curve. This curve is then used to determine an unknown concentration from the percent retention calculated from radioactivity counts.

In principle, the total radioactivity is determined by the amount of radioactivity labeled ligand or analog used for the preparation of the reaction mixture. However, to avoid inaccuracies due to imprecise application of the labeled component, it may be preferable to establish the total radioactivity experimentally. This may be done either before or after the selective determination of the radioactivity of the intake region of the adsorbent column. The total radioactivity may be determined after incubation and before the introduction of the absorbent column into the reaction mixture. Alternatively, where the selective counting of the intake tip region is effected by partial shielding of the counter well, it is also possible, in accordance with the present invention, to measure the total radioactivity after the separation of the components. To this end, after the counting of the intake region of the column is completed the shield is withdrawn from the well whereby the entire body becomes exposed to the counter which latter then responds to the total radioactivity.

The present invention also provides a method for determining the ligand binding capacity of a liquid medium. In such an assay, the liquid medium is suspected of containing a binding agent for the ligand. For example, the method according to the invention can be modified for the performance of the so called "T-3 Uptake Test". In this test, the thyroid hormone in serum is indirectly assayed by determining the available binding sites on thyroid binding globulin (TBG) present in the serum. In this test, it is assumed that the amount of TBG in normal sera is relatively constant and that it binds most of the available thyroid hormone. When labeled T-3 (triiodothyronine) is added to a serum sample, it will be bound by the TBG in proportion to the residual binding sites available thereon. Thus, if it is found that a large amount of labeled T-3 is bound by the serum, this indicates a large number of available binding sites and hence a low level of thyroid hormone, and vice versa. Measurement of the unbound labeled T-3 can thus be related to thyroid function. In the clinical application of the T-3 uptake test, it suffices in many cases to determine the T-3 uptake ratio in comparison with a standard normal serum. This ratio can be derived by dividing the partial count (as defined above) obtained from the unknown sample by the partial count of a standard serum sample which has been subjected to a parallel, identical assay procedure.

In preferred embodiment, the determination of ligand binding capacity in the liquid medium, usually aqueous, is carried out by an improved radioassay method of the type wherein said aqueous medium is mixed with a radiolabeled form of said ligand or of a binding analog thereof and the resulting mixture is incubated to form a bound-species of said radiolabeled ligand or analog wherein such is bound to a binding agent of said aqueous medium and a free species of said radiolabeled ligand or analog wherein such is not bound to said binding agent, wherein said bound-species and said free-species are separated, and wherein the radioactivity of one of said separated bound-species and said free-species is measured. The improvement of the present invention comprises accomplishing said separation of said bound-species and said free-species by contacting said reaction mixture with a column of a capillarily absorbent adsorbent material which is selective for one of said bound-species and said free-species and which is capable of drawing all of said return mixture thereinto by capillary action whereby said bound-species and said free-species are separated along said column.

The present invention also provides a test kit for carrying out the present method. A test kit is provided for determining a ligand in a liquid medium, comprising (1) said ligand, or a binding analog thereof, incorporated with a label, such as a radioactive atom, (2) a binding agent for said ligand, such as an antibody, and (3) a column of an adsorbent material selective for one of said ligand or the binding complex of said ligand and said binding agent. Also provided is a test kit for determining the ligand binding capacity of a liquid medium, comprising (1) said ligand, or a binding analog thereof, incorporated with a label, such as a radioactive atom, and (2) a column of an adsorbent as discussed above. The test kit may additionally comprise an aqueous buffer solution and ligand standards.

The present invention will now be illustrated, but is not intended to be limited, by the following examples.

PREPARATION OF CROSS-LINKED POLYVINYL ALCOHOL

Hydrochloric acid (concentrated, 5 ml) was added to a stirred solution of 10 grams of cold water soluble crystalline Type II polyvinyl alcohol (PVA) (catalog No. P-8136, Sigma Chemical Co., St. Louis Missouri, U.S.A.) in water (600 ml). The resulting viscous solution was stirred with a high-powered stirrer and heated to 65° C. Glutaraldehyde (25% aqueous solution, 10 ml) was added and the reaction mixture was stirred at 65° C. for 20 min. The resulting insoluble, cross-linked PVA was filtered and washed with distilled water until the pH of the washing was neutral. The wet cake was washed with ethanol or acetone and air-dried. The yield of the granular, white polymer was 11.0 g. No melting, softening or decomposition was observed on heating to 260° C. It was found insoluble in water and in organic solvents, including refluxing dimethylformamide (DMF).

PREPARATION OF ADSORBENT COLUMNS

Plastic tubes about 8 cm long and about 0.5 cm inner diameter were used. A porous retainer disc was pressed into the bottom of each tube in such a way that it would be flush with the bottom but would not fall out. The column was then evenly filled with about 0.1 g of a dry adsorbent (such as cross-linked polyvinyl alcohol prepared as above) to a height of about 6 cm and a second porous disc was pushed coaxially into firm contact with the top of the adsorbent bed.

EXAMPLE 1

Radioimmunoassay for Thyroxine (T-4)

In order to perform a radioimmunoassay for T-4, the following reagents, all dissolved in tris-maleate buffer pH 7.4 [prepared by dissolving 2.85 g tris-(hydroxymethyl)-aminomethane, 1.2 g maleic acid and 0.43 g ethylenediamine tetraacetic acid in 290 ml of distilled water] were added step-wise to test tubes:
(1) 200 μl $^{125}$I-T-4 (about 100 kcpm)
(2) 200 μl T-4 standard (diluted 1:4 in concentration range of 4-60 μg/liter) or a 1:4 diluted clinical serum sample
(3) 50 μl ANS solution (8-anilino-1-napthalene sulfonic acid, ammonium salt, 4 g/liter)
(4) 200 μl anti-T-4 antibody (dissolved in 5 ml buffer).

The test tubes were gently shaken after each of step 3 and step 4 to ensure thorough mixing of the reagents. Then, following 20 minutes of incubation at room temperature, an adsorbent column, with cross-linked PVA as adsorbent, prepared as above, was placed vertically in the test tube and the reaction mixture allowed to ascend in the dry cross-linked polyvinyl alcohol. When all the reaction mixture had been adsorbed, the total radioactivity (total count) was determined. For this purpose the adsorbent column was introduced into the well of a gamma counter without any metal shield. The radioactivity of the intake portion of the column (holding free $^{125}$I-T-4) was then determined (partial count) using the metal shield to prevent the radioactivity from the remaining part of the column from being counted. The percent retention of each column was calculated using the equation:

$$\text{percent retention} = \frac{\text{partial count}}{\text{total count}} \times 100$$

Figure 2:
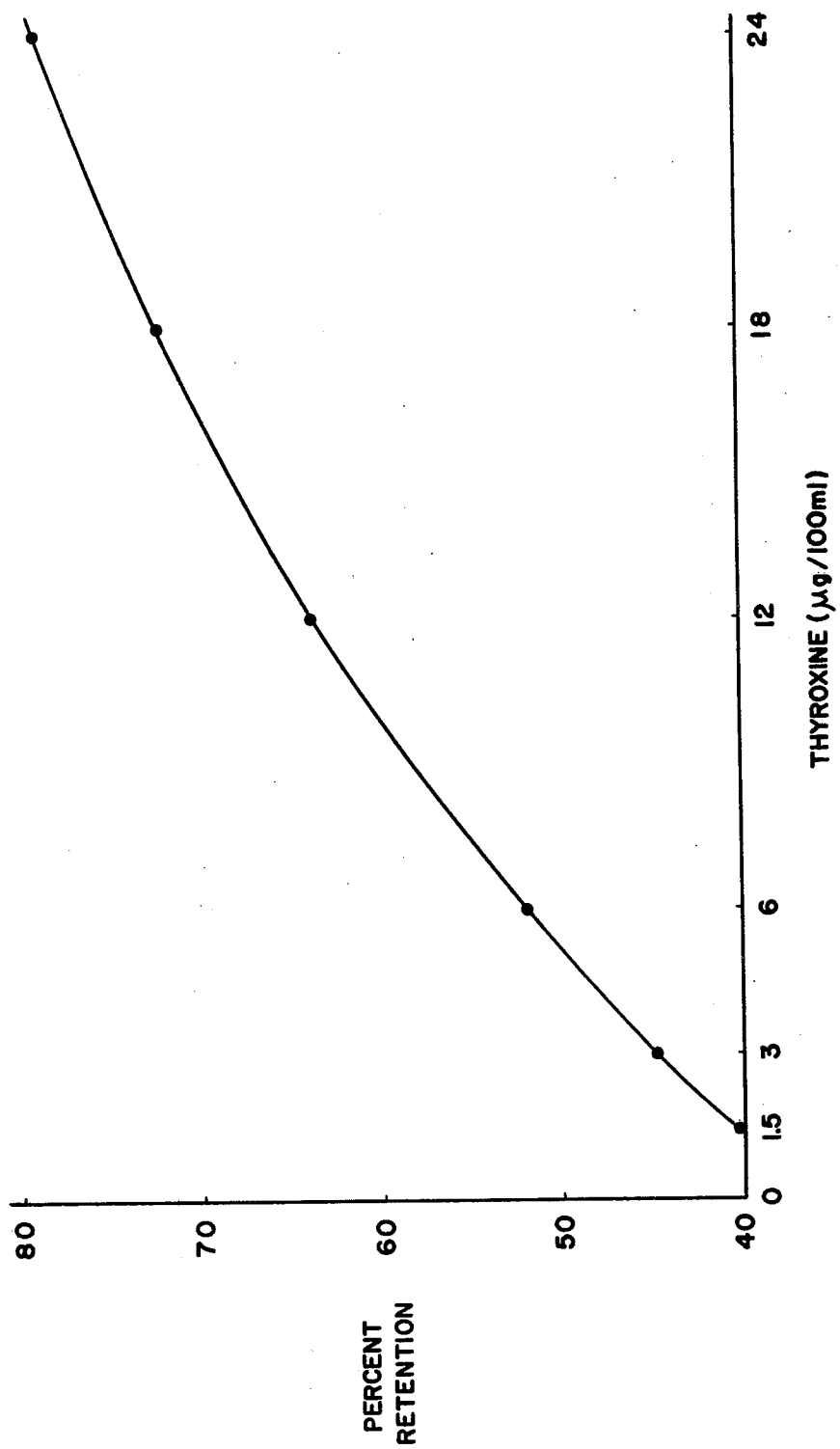
FIG. 2 is an illustrative standard curve obtained by plotting the percent retention against known amounts of thyroxine using cross-linked polyvinyl alcohol columns.

A standard curve was obtained by plotting the percent retention values versus the corresponding concentrations of thyroxine standard (FIG. 2).

Unknown amounts of T-4, e.g., in serum, can be determined in the above manner with the aid of the standard curve of FIG. 2. Using this standard curve two reference sera identified as Led-I and Led-II obtained from Lederle Diagnostics, American Cyanamid Company, Pearl River, N.Y., U.S.A. were tested in duplicate.

Results were obtained as follows:
Led-I: 7.0 and 7.9 µg/100 ml (expected value=8-11 µg/100);
Led-II: 16.5 and 17.6 µg/100 ml (expected value=16-.9-25.5 µg/100 ml).

EXAMPLE 2

Radioimmunoassay for Digoxin

Cross-linked polyvinyl alcohol adsorbent columns were prepared as described above. The buffer used in this test was a phosphate buffer, pH 7.4 (6.25 g/liter sodium biphosphate, pH adjusted with sodium hydroxide solution).

In order to perform a radioimmunoassay for digoxin, the following reagents were added step-wise to test tubes:
1. 200 µl $^{125}$I-digoxin (27 kcpm)
2. 150 µl standard digoxin. The standards were prepared by diluting 1 ml of stock solutions having concentrations of 0.5, 2.0 and 5.0 µl/ml with one ml of normal serum and one ml buffer. The standards were thus diluted 1:3.
3. 150 µl antidogixin rabbit antiserum in phosphate buffer containing 0.2% bovine serum albumin.

The reaction mixture was incubated at room temperature for 40 minutes in the test tube. Then an adsorbent column as in Example 1 was placed vertically in the test tube and the reaction mixture allowed to ascend into the dry cross-linked polyvinyl alcohol. When all the reaction mixture had been adsorbed, total and partial radioactivity counts were performed and the percent retention calculated as in Example 1, and a standard curve was obtained in a similar manner (FIG. 3).

Figure 3:
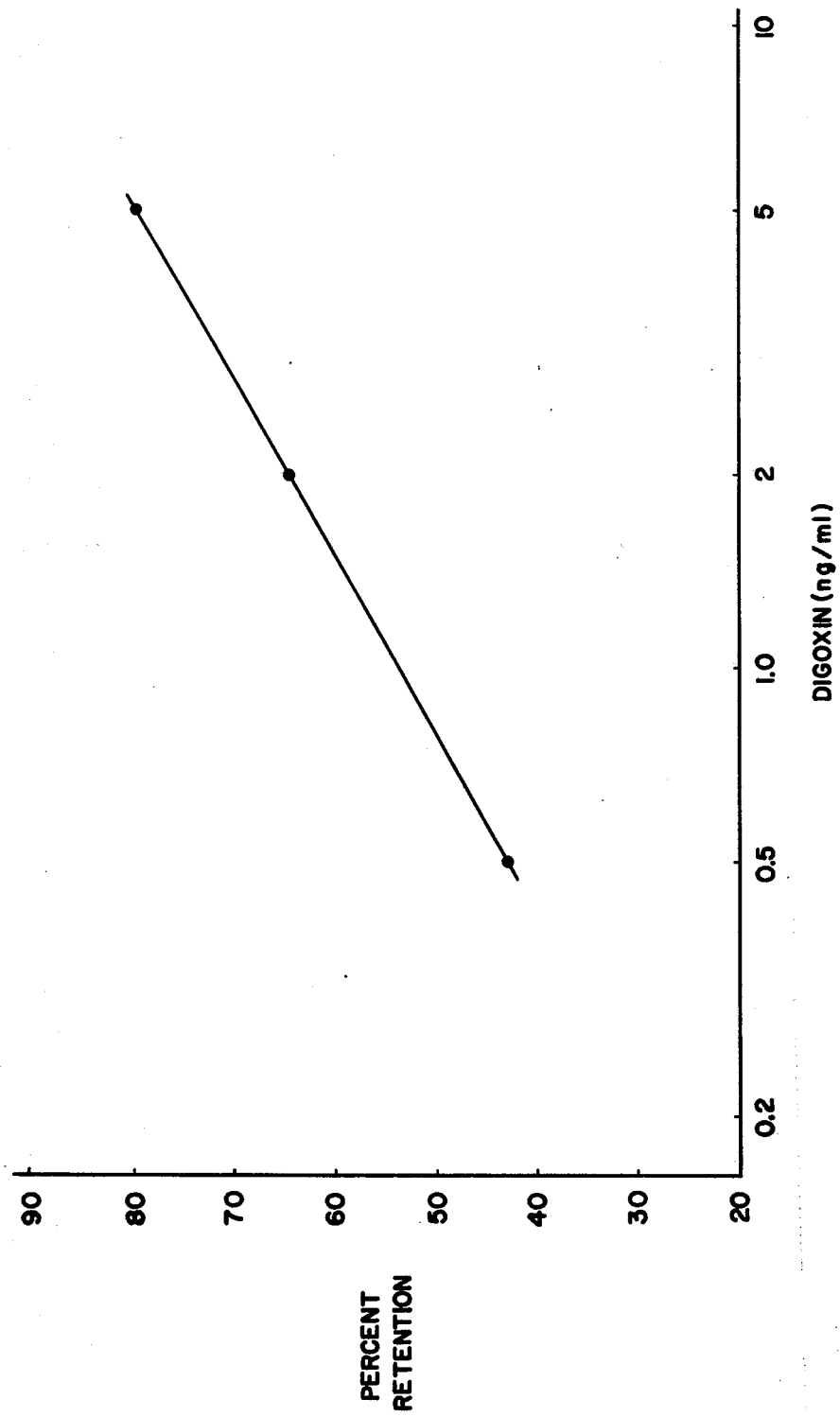
FIG. 3 is an illustrative standard curve obtained by plotting the percent retention against known amounts of digoxin using cross-linked polyvinyl alcohol columns.

Unknown amounts of digoxin, e.g., in serum, can be determined in the above manner with the aid of the standard curve of FIG. 3.

Using this standard curve the two reference sera (Led-I and Led-II) were tested in duplicate. Results were obtained as follows:
Led-I: 1.0 ng/ml (expected value-0.8-1.2 ng/ml).
Led II: 3.8 ng/ml (expected value-2.5-4.0 ng/ml).

EXAMPLE 3

Radioassay for Triiodothyronine (T-3) Uptake

Cross-linked polyvinyl alcohol adsorbent columns were prepared as described above. The buffer used in this test was made by dissolving citric acid (14.4 g) and sodium biphosphate (NaH$_2$PO$_4$.8H$_2$O) (43.75 g) and 37% formaldehyde solution (2.7 ml) in distilled water (1 liter).

The test was performed by adding the following reagents to a test tube:
1. 200 µl $^{125}$I-T-3 (in citric acid buffer, 120 kcpm)
2. 20 µl serum (standard or clinical sample).

The test tube was shaken gently to ensure thorough mixing of the contents. An adsorbent column as in Example 1 was then placed vertically in the test tube and the reaction mixture allowed to ascend in the cross-linked polyvinyl alcohol. Immediately after all the reaction mixture had been absorbed, 200 µl of buffer was added to the test tube and this was also allowed to ascend in the column.

A partial radioactivity count of the intake portion of the column was performed using the metal shield.

The result was calculated as follows:

$$\frac{\text{counts of clinical sample column}}{\text{counts of standard serum column}} = x$$

x=1 was normal, x<1 was low, x>1 was high.

Results obtained for low, normal, and high sera in terms of known T-3 uptake values were as follows: 0.6, 0.9 and 1.5.

EXAMPLE 4

Radioimmunoassay for Thyroxine (T-4)

The procedure of Example 1 was repeated with the single difference that instead of the cross-linked PVA columns there were used columns of the same type filled with "Sephadex G-10" brand cross-linked dextran (manufactured by Pharmacia Fine Chemicals, Uppsala, Sweden).

Figure 4:
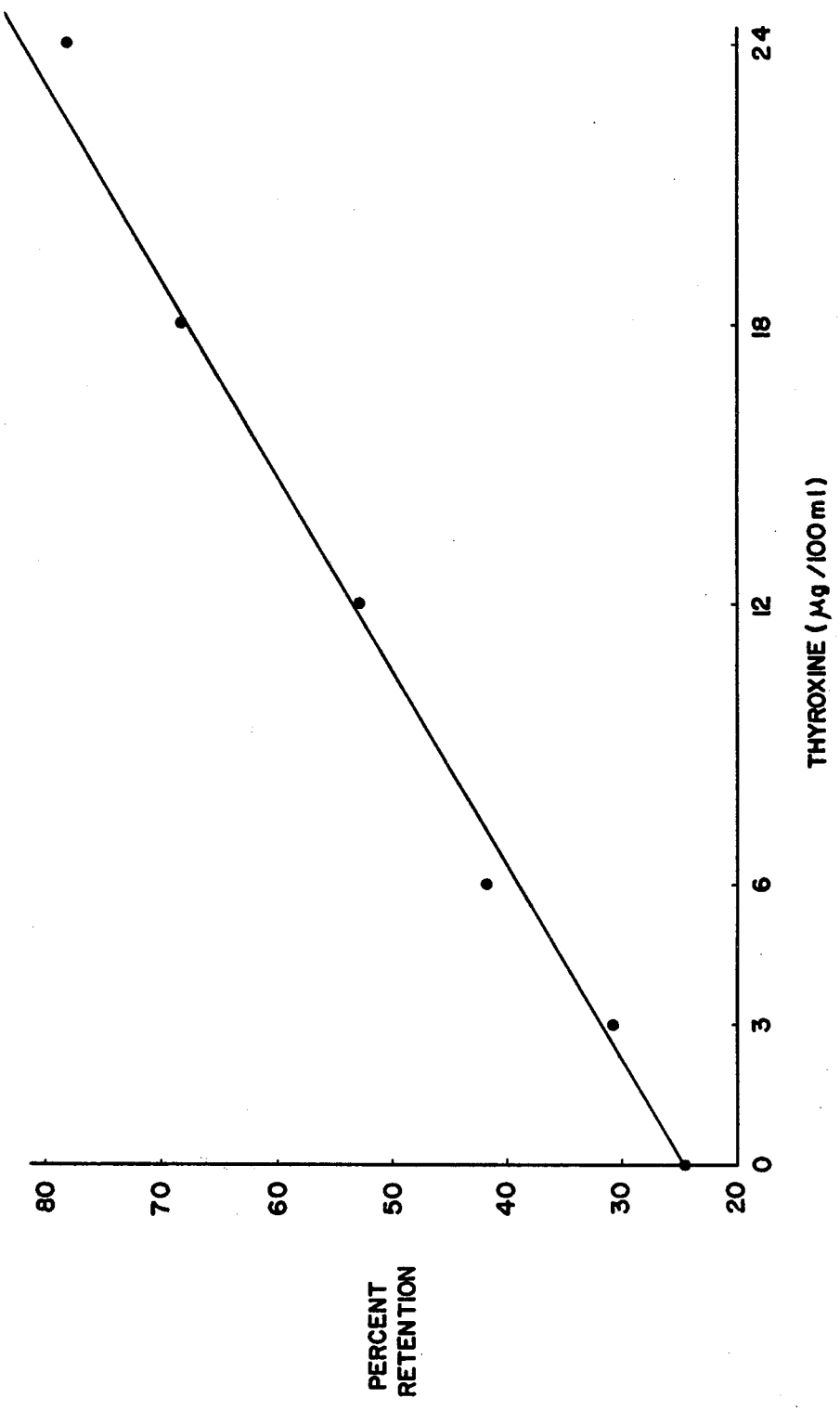
FIG. 4 is an illustrative standard curve obtained by plotting the percent retention against known amounts of thyroxine using cross-linked dextran columns.

The percent retention was calculated as in Example 1 and the percent retention values obtained were plotted versus the corresponding concentrations of the T-4 standards. The standard curve obtained is shown in FIG. 4.

Unknown amounts of T-4, e.g., in serum, were determined in the above manner with the aid of the standard curve.

EXAMPLE 5

Radioimmunoassay for Digoxin

The procedure of Example 2 was repeated substituting the cross-linked PVA columns with dextran columns as described in Example 4.

Figure 5:
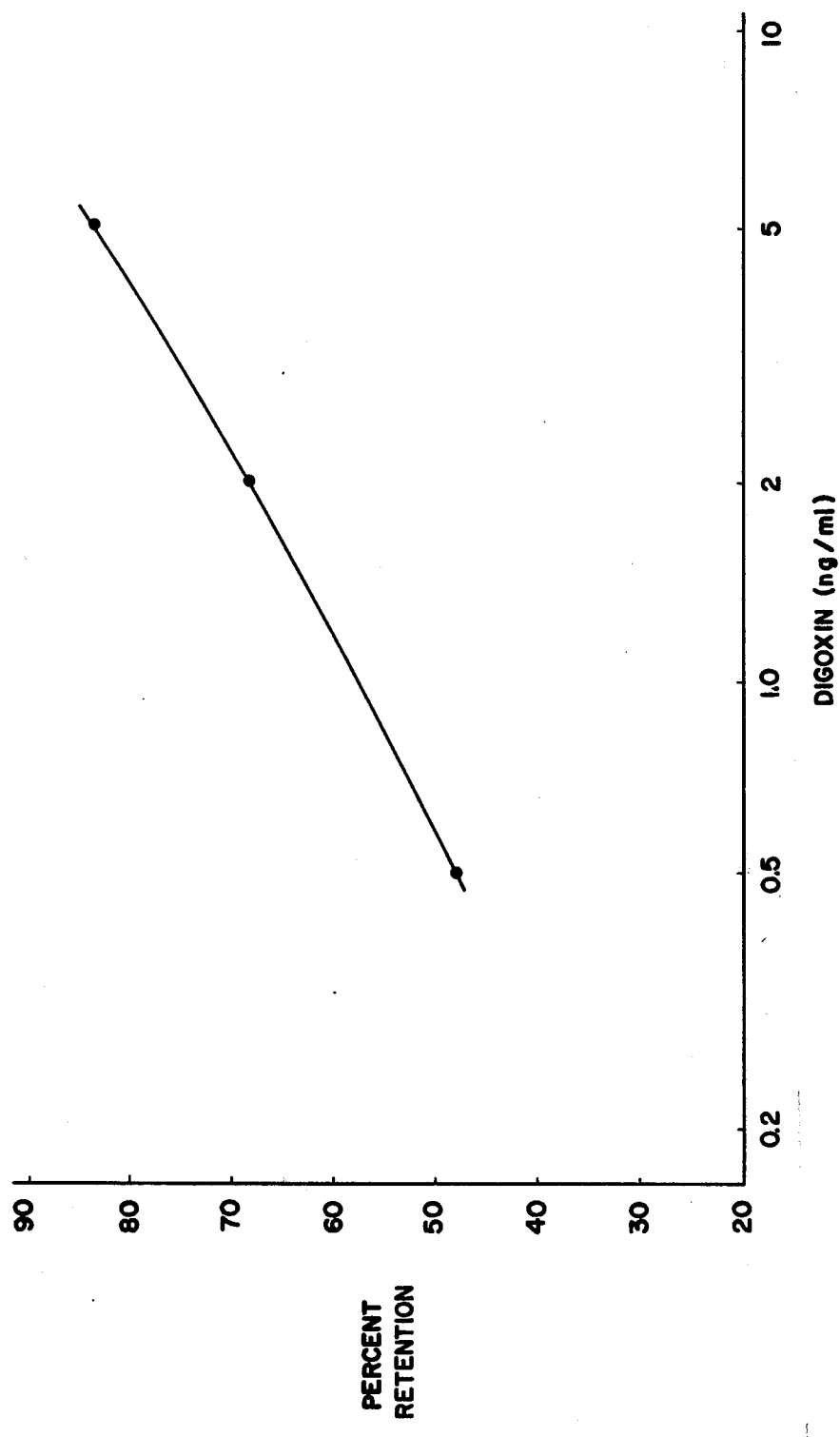
FIG. 5 is an illustrative standard curve obtained by plotting the percent retention against known amounts of digoxin using cross-linked dextran columns.

Total and partial radioactivity counts were performed and the percent retention calculated as described in Example 1. With the aid of the obtained standard curve shown in FIG. 5, unknown amounts of digoxin, e.g., in serum, were determined in the above manner.

EXAMPLE 6

Radioimmunoassay for Thyroxine (T-4)

A. Preparation of formaldehyde treated starch

To a suspension of 100 g of starch (Starch Soluble Analar brand, The British Drug House, Poole, England) in 200 ml of water, there were added 45 ml of a 40% aqueous formaldehyde solution, followed by 10 ml of concentrated hydrochloric acid. The mixture was stirred at room temperature for 18 hours and then filtered. The solid product was washed repeatedly with water until it was pH neutral, then washed with acetone and dried.

B. Preparation of adsorbent columns

The procedure for preparing the columns described above was followed, except that the columns were filled with formaldehyde treated starch, prepared as described in part A.

C. Radioimmunoassay for T-4

The following reagents, all dissolved in tris-maleate buffer were added step-wise to test tubes:

(1) 100 µl $^{125}$I-T-4 (approximately 90 kcpm).
(2) 100 µl T-4 standard (diluted 1:4 in concentration range of 4-60 µg/liter) or a 1:4 diluted clinical serum sample.
(3) 50 µl ANS solution (8-anilino-1-naphthalene sulfonic acid, ammonium salt, 4 g/l).
(4) 100 µl anti-T-4 antibody (dissolved in 3 ml buffer).

Figure 6:
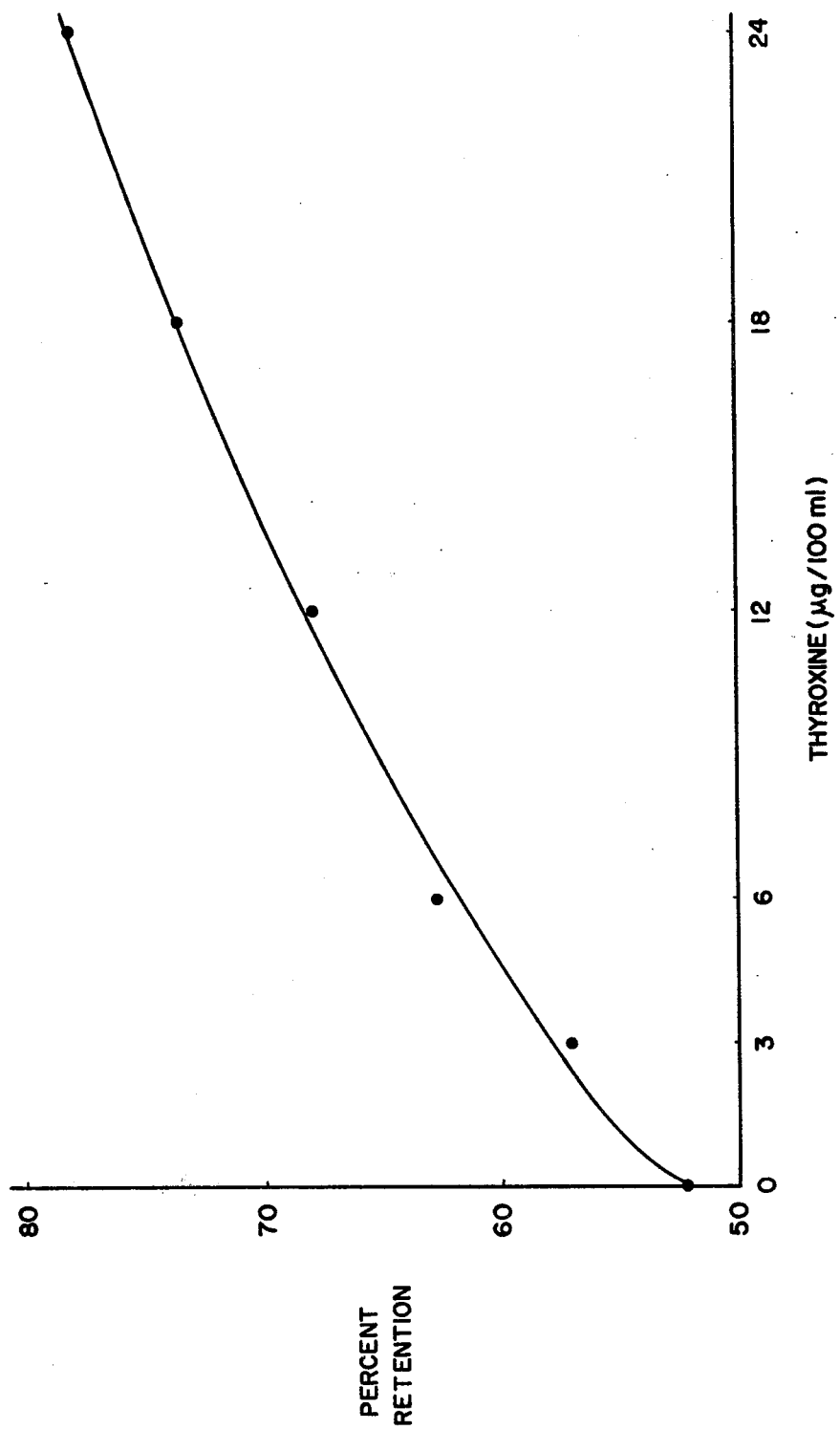
FIG. 6 is an illustrative standard curve obtained by plotting the percent retention against known amounts of thyroxine using columns filled with formaldehyde treated starch.

The procedure of Example 1 was accurately repeated, and by plotting the calculated percent retention values the standard curve shown in FIG. 6 was obtained.

EXAMPLE 7

Radioimmunoassay for Digoxin

The procedure of Example 2 was followed, substituting the cross-linked PVA columns with columns filled with starch (about 0.5 g) (Starch Soluble Analar brand, The British Drug House, Poole, England).

The following volumes of reagents were used:
(1) 150 µl $^{125}$I-digoxin (27 kcpm).
(2) 50 µl standard digoxin or serum sample.
(3) 100 µl antidigoxin rabbit antiserum.

Figure 7:
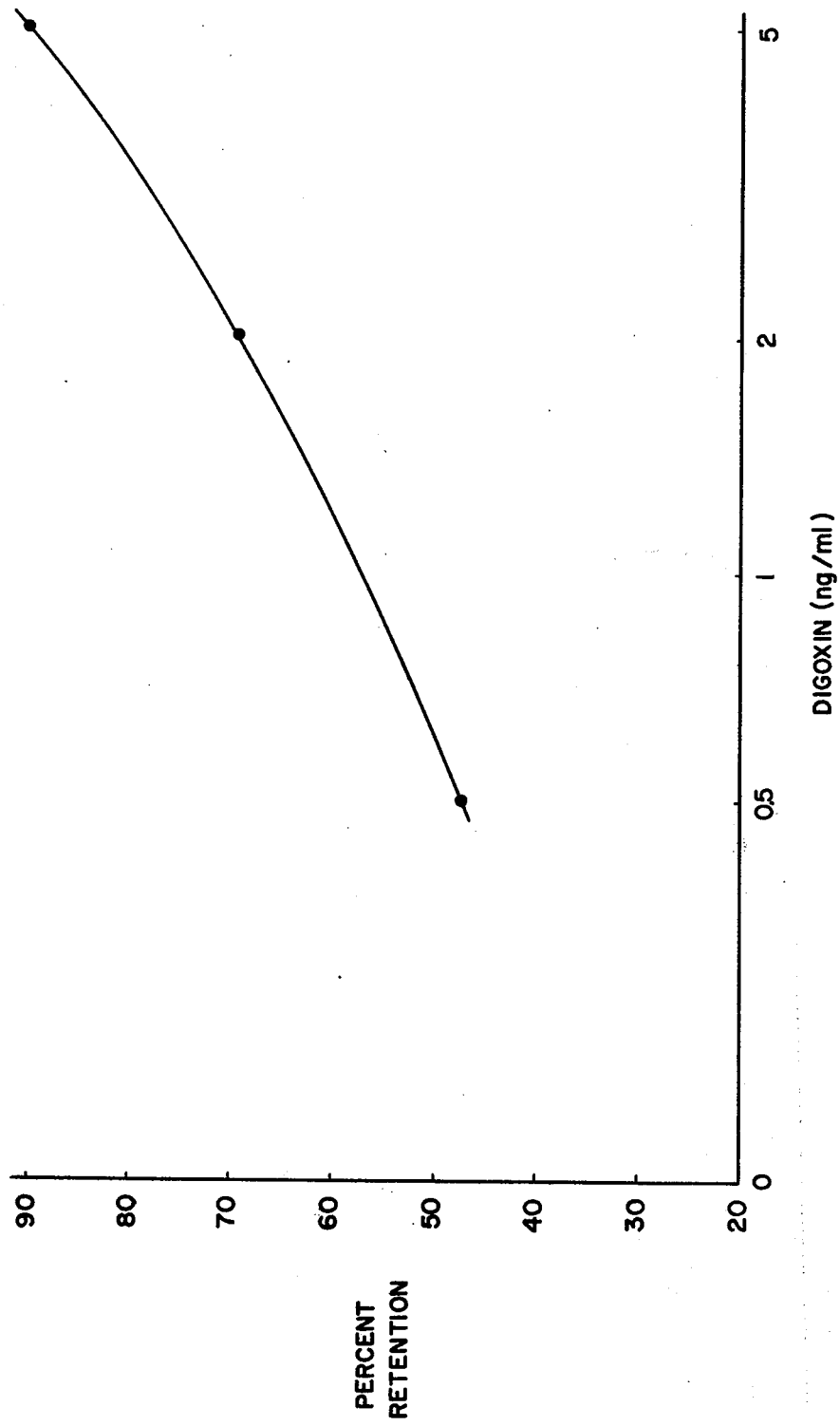
FIG. 7 is an illustrative standard curve obtained by plotting the percent retention against known amounts of digoxin using starch filled columns.

The standard curve obtained is shown in FIG. 7.

With the aid of the standard curve, two clinical reference sera were tested (triplicate assays) and the results compared with digoxin assays using standard methods. The following results were obtained:

Serum sample No. 1:1.2 ng/ml (expected value 1.0-1.5 ng/ml)
Serum sample No. 2:3.7 ng/ml (expected value 2.0-5.0 ng/ml)

EXAMPLE 4

Radioimmunoassay for Digoxin

The procedure was similar to that of Example 2, substituting the cross-linked PVA columns with columns filled with silica gel (200-400 mesh, Kieselgel 60, Catalog No. 9385, E. Merck, Darmstadt, West Germany).

The following volumes of reagents were used:
(1) 200 µl $^{125}$I-digoxin.
(2) 150 µl standard digoxin or serum sample.
(3) 150 µl antidigoxin rabbit serum.

Figure 8:
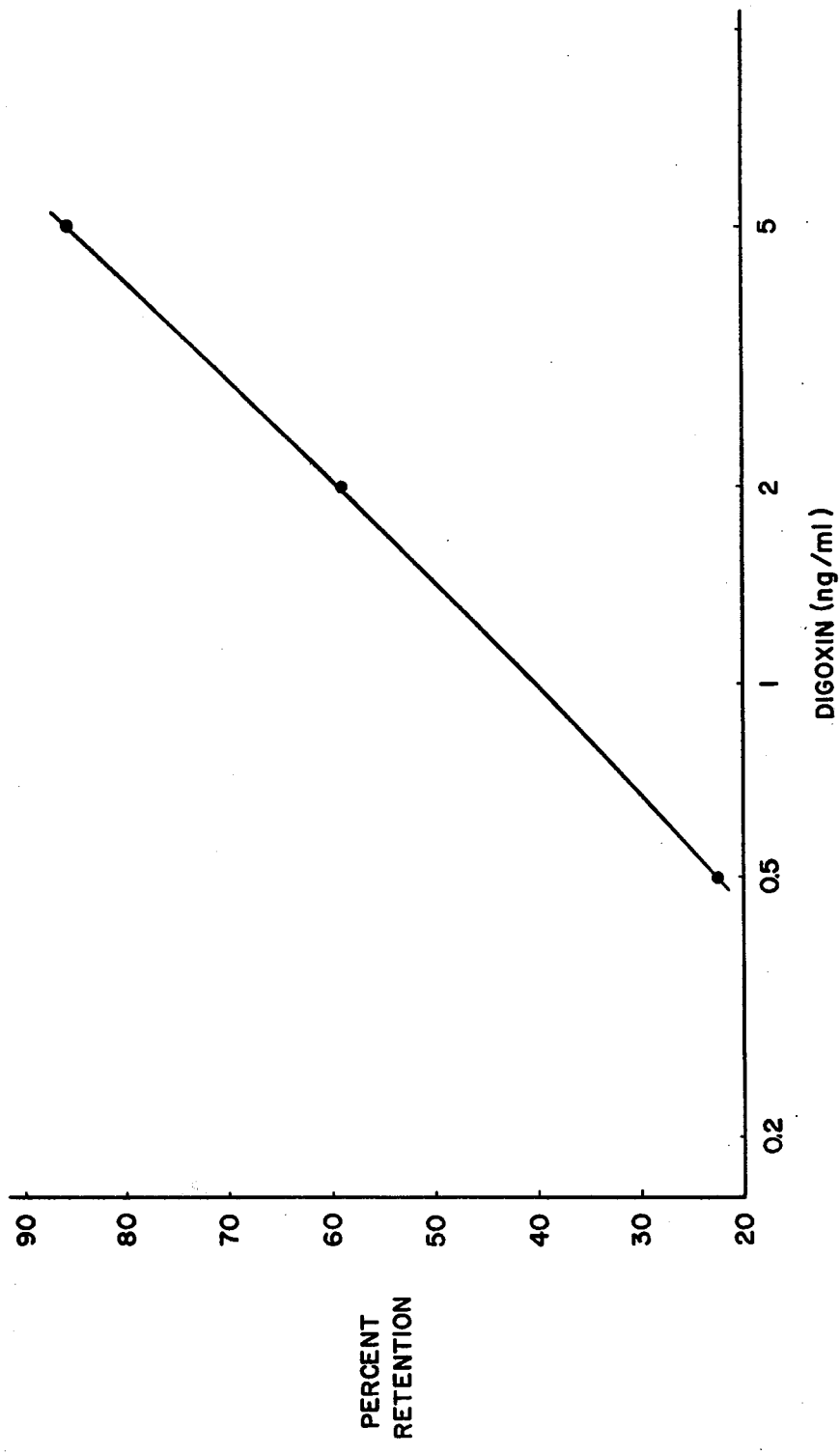
FIG. 8 is an illustrative standard curve obtained by plotting the percent retention against known amounts of digoxin using silica gel columns.

The reaction mixture was allowed to incubate at room temperature for 50 minutes, whereafter an adsorbent column was placed in the test tube and the reaction mixture was allowed to ascend into the dry silica gel. When all the reaction mixture had been adsorbed, a further volume of 400 µl of the phosphate buffer solution was added to the test tube and allowed to ascend into the silica gel column. Total and partial radioactivity counts were performed and partial retention values calculated as in Example 1. The standard curve obtained is shown in FIG. 8.

With the aid of the standard curve 20 replicate tests were performed on a pooled clinical serum. The following resuls were obtained:

| Concentration of Digoxin | |
|---|---|
| Found: | 2.9 ng/µl |
| determined by other test method*: | 2.5-3.0 ng/µl |
| Coefficient of variance = 12% | |

*(Digoxin Test Kit, catalog no. 070-06, Schwarz Mann, Orangeburg, New York, U.S.A.)

EXAMPLE 9

Radioassay for Triiodothyronine (T-3) Uptake

Glass Pasteur pipettes were cut so as to form a column about 7 cm long having an inner diameter of about 6 mm and a constriction at the bottom end. A small plug of glass wool was inserted down to the bottom of the column and the column was filled with fine silica gel (200-400 mesh, Kieselgel 60, catalog no. 9385, E. Merck, Darmstadt, West Germany). A second plug of glass wool was inserted into the column in order to retain the contents in place.

The procedure, reagents and volumes were the same as in Example 3, except that after the reaction mixture had been absorbed, 500 µl of distilled water (instead of the 200 µl of buffer in Example 3) were added to the test tube and allowed to ascend in the column.

The partial radioactivity count was performed and the T-3 uptake ratio (x) calculated as in Example 3. The results obtained for low, normal, and high sera in terms of known T-3 uptake value were as follows:

| Serum: | Standard | Low | Normal | High |
|---|---|---|---|---|
| Counts: | 26.9 | 19.3 | 27.3 | 45.9 |
| T-3 uptake ratio calculated | | 0.72 | 1.02 | 1.71 |
| T-3 uptake ratio determined by known method* | | 0.70 | 1.02 | 1.37 |

(Trilute brand T-3 Uptake Test Kit, Ames Company Division of Miles Laboratories, Inc., Elkhart, Indiana, U.S.A.)

What is claimed is:

1. In a specific binding assay method for determining a ligand in or the ligand binding capacity of a liquid medium,
   wherein for determining said ligand, said liquid medium is combined with assay reagent means comprising (i) as labeled component, said ligand or a binding analog thereof incorporated with a label and (ii) a binding reagent for said ligand; or
   wherein for determining the ligand binding capacity of said liquid medium suspected of containing a binding agent for said ligand, said liquid medium is combined with assay reagent means comprising, as labeled component, said ligand or a binding analog thereof incorporated with a label, thereby to form a binding reaction mixture having a bound-species as said labeled component bound to said binding reagent and a free-species as said labeled component not bound to said binding agent, wherein said bound-species and said free-species are separated, and wherein said label is measured in one of the separated species;

the improvement which comprises accomplishing said separation of said bound-species and said free-species by contacting at least a portion of said binding reaction mixture, a predetermined time after formation thereof, with a column comprising an adsorbent material which is both selective for binding one of said bound-species and said free-species and capillarily absorbent relative to said reaction mixture whereby said at least a portion of said reaction mixture is drawn into said column by capillary action and said bound-species and said free-species are separated along said column.

2. The method of claim 1 wherein after said portion or all of said reaction mixture has been drawn into said column of adsorbent material, the same end of said column as that contacted with said reaction mixture is contacted with a volume of liquid inert with respect to the selective adsorption of said one of said bound-species and said free-species, and said inert liquid is drawn into said column to enhance the separation thereof along said column.

3. The method of claim 1 wherein the volume of said adsorbent column is sufficiently large to allow capillary absorption of all of said reaction mixture thereinto.

4. The method of claim 1 wherein said adsorbent material is selected from the group consisting of cross-linked polyvinyl alcohol, cross-linked dextran, starch, and silica gel.

5. The method of claim 1 wherein said ligand to be determined is selected from the group consisting of antigens and anitbodies thereto; heptens and antibodies thereto; and hormones, vitamins, metabolites and pharmacological agents, and their receptors and binding substances.

6. The method of claim 1 wherein said label is a gamma-emitting radioactive atom.

7. The method of claim 1 wherein said binding agent is an antibody.

8. In a radioimmunoassay method for determining a ligand in an aqueous medium, wherein said aqueous medium is mixed with a radiolabeled form of said ligand or of a binding analog thereof and with an antibody for said ligand and the resulting reaction mixture is incubated for a predetermined period of time to form a bound-species of said radiolabeled ligand or analog wherein such is bound to said antibody and a free-species of said radiolabeled ligand or analog wherein such is not bound to said antibody, wherein said bound-species and said free-species are separated, and wherein the radioactivity of one of said separated bound-species and said free-species is measured, the improvement which comprises accomplishing said separation of said bound-species and said free-species by contacting said reaction mixture, after said predetermined incubation period, with a column comprising an adsorbent material which is selective for binding one of said bound-species and said free-species, capillarily absorbent relative to said reaction mixture, and of sufficient volume to be capable of drawing all of said reaction mixture thereinto by capillary action, whereby said bound-species and said free-species are separated along said column.

9. The method of claim 8 wherein after all of said reaction mixture has been drawn into said column of adsorbent material, the same end of said column as that contacted with said reaction mixture is contacted with a volume of liquid inert with respect to the selective adsorption of said one of said bound-species and said free-species to enhance the separation thereof along said column.

10. The method of claim 9 wherein said inert liquid is water or an aqueous buffer solution.

11. The method of claim 8 wherein the measurement of radioactivity of one of said bound-species and said free-species is accomplished by placing said column in a well of a radioactivity counting apparatus with that portion of said column containing the other of said bound-species and said free-species being selectively shielded from said counting apparatus by a radio-opaque material.

12. The method of claim 11 wherein said portion of said column to be shielded is so shielded by use of a well-liner composed of radio-opaque material.

13. The method of claim 8 wherein said adsorbent column is in the form of an elongated tube containing a volume of said adsorbent material held in position by retaining means.

14. The method of claim 8 wherein said adsorbent material is cross-linked polyvinyl alcohol.

15. The method of claim 8 wherein said adsorbent material is cross-linked dextran.

16. The method of claim 8 wherein said adsorbent material is formaldehyde treated starch.

17. The method of claim 8 wherein said adsorbent material is silica gel.

18. The method of claim 8 wherein said ligand to be determined is thyroxine.

19. The method of claim 18 wherein adsorbent material is cross-linked polyvinyl alcohol, cross-linked dextran, or starch.

20. The method of claim 8 wherein said ligand to be determined is digoxin.

21. The method of claim 20 wherein said adsorbent material is cross-linked polyvinyl alcohol, cross-linked dextran, starch, or silica gel.

22. In a radioassay method for determining the ligand binding capacity of an aqueous medium due to the presence of a binding agent for said ligand therein, wherein said aqueous medium is mixed with a radiolabeled form of said ligand or of a binding analog thereof and the resulting mixture is incubated for a predetermined period of time to form a bound-species of said radiolabeled ligand or analog wherein such is bound to said binding agent from said aqueous medium and a free-species of said radiolabeled ligand or analog wherein such is not bound to said binding agent, wherein said bound-species and said first-species are separated, and wherein the radioactivity of one of said separated bound-species and said free-species is measured, the improvement which comprises accomplishing said separation of said bound-species and said free-species by contacting said reaction mixture, after said predetermined incubation period, with a column comprising an adsorbent material which is selective for binding one of said bound-species and said free-species, capillarily absorbent relative to said reaction mixture, and of sufficient volumne to be capable of drawing all of said reaction mixture thereinto by capillary action, whereby said bound-species and said free-species are separated along said column.

23. The method of claim 22 wherein after all of said reaction mixture has been drawn into said column of adsorbent material, the same end of said column as that contacted with said reaction mixture is contacted with a volume of liquid inert with respect to the selective adsorption of said one of said bound-species and said free-species to enhance the separation thereof along said column.

24. The method of claim 23 wherein said inert liquid is water or an aqueous buffer solution.

25. The method of claim 22 wherein the measurement of radioactivity of one of said bound-species and said free-species is accomplished by placing said column in a well of a radioactivity counting apparatus with that portion of said column containing the other of said bound-species and said free-species being selectively shielded from said counting apparatus by a radio-opaque material.

26. The method of claim 25 wherein said portion of said column to be shielded is so shielded by use of a well-liner composed of radio-opaque material.

27. The method of claim 22 wherein said adsorbent column is in the form of an elongated tube containing a volume of said adsorbent material held in position by retaining means.

28. The method of claim 22 wherein said adsorbent material is cross-linked polyvinyl alcohol.

29. The method of claim 22 wherein said adsorbent material is cross-linked dextran.

30. The method of claim 22 wherein said adsorbent material is formaldehyde treated starch.

31. The method of claim 22 wherein said adsorbent material is silica gel.

32. The method of claim 22 wherein the ligand binding capacity of said aqueous medium is the capacity of said medium to bind triiodothyronine.

33. The method of claim 32 wherein said adsorbent material is cross-linked polyvinyl alcohol or silica gel.

34. A test kit for determining a ligand in a liquid medium, comprising, in a packaged combination,
(a) one of more containers holding
  (1) said ligand or a binding analog thereof incorporated with a label, and
  (2) a binding agent for said ligand, and
(b) a column of an adsorbent material which is both capillarily absorbent relative to said liquid medium and selective for binding one of (i) said labeled ligand or binding analog and (ii) the binding complex of said labeled ligand or binding analog with said binding agent.

35. The test kit of claim 34 which additionally comprises a container of an aqueous buffer solution and at least one container of a ligand standard.

36. The test kit of claim 34 wherein said adsorbent column is in the form of an elongated tube containing a volume of said adsorbent material held in position by retaining means.

37. The test kit of claim 34 wherein said adsorbent material is selected from the group consisting of cross-linked polyvinyl alcohol, cross-linked dextran, starch, and silica gel.

38. The test kit of claim 34 wherein said label is a radioactive atom.

39. The test kit of claim 34 wherein said binding agent is an antibody.

40. A test kit for determining the ligand binding capacity of a liquid medium due to the presence of a binding agent for said ligand therein, comprising, in a packaged combination,
(a) a container holding said ligand or a binding analog thereof incorporated with a label, and
(b) a column of an adsorbent material which is both capillarily absorbent relative to said liquid medium and selective for binding one of (i) said labeled ligand or binding analog and (ii) the binding complex of said labeled ligand or binding analog with said binding agent.

41. The test kit of claim 40 which additionally comprises a container of an aqueous buffer solution and at least one container of a ligand binding capacity standard.

42. The test kit of claim 40 wherein said adsorbent column is in the form of an elongated tube containing a volume of said adsorbent material held in position by retaining means.

43. The test kit of claim 40 wherein said adsorbent material is selected from the group consisting of cross-linked polyvinyl acohol, cross-linked dextran, starch, and silica gel.

44. The test kit of claim 40 wherein said label is a radioactive atom.